United States Patent
Holmström et al.

(10) Patent No.: US 6,188,931 B1
(45) Date of Patent: Feb. 13, 2001

(54) ELECTRODE LEAD WITH TEMPORARY INCREASED STIFFNESS DURING INGROWTH

(75) Inventors: Nils Holmström, Järfälla; Martin Obel, Danderyd, both of (SE)

(73) Assignee: Pacesetter AB, Järfälla (SE)

(*) Notice: Under 35 U.S.C. 154(b), the term of this patent shall be extended for 0 days.

(21) Appl. No.: 09/319,403
(22) PCT Filed: Nov. 28, 1997
(86) PCT No.: PCT/SE97/02002
§ 371 Date: Jul. 26, 1999
§ 102(e) Date: Jul. 26, 1999
(87) PCT Pub. No.: WO98/24506
PCT Pub. Date: Jun. 11, 1998

(30) Foreign Application Priority Data

Dec. 4, 1996 (SE) ................................... 9604477

(51) Int. Cl.$^7$ ........................................ A61N 1/05
(52) U.S. Cl. ............................................. 607/123
(58) Field of Search .................... 607/122, 123, 607/118, 126; 600/374, 375

(56) References Cited

U.S. PATENT DOCUMENTS

| 4,154,247 | 5/1979 | O'Neill . |
| 5,376,109 | 12/1994 | Lindegren et al. . |
| 5,476,499 | 12/1995 | Hirschberg . |
| 5,628,778 | * 5/1997 | Kruse et al. ...................... 607/123 |

FOREIGN PATENT DOCUMENTS

| 0 783 900 | 7/1997 | (EP) . |
| 0 784 994 | 7/1997 | (EP) . |
| 0 784 995 | 7/1997 | (EP) . |
| WO 80/02801 | 12/1980 | (WO) . |

* cited by examiner

Primary Examiner—George R. Evanisko
(74) Attorney, Agent, or Firm—Schiff Hardin & Waite

(57) ABSTRACT

An implantable lead for an implantable active device, such as a pacemaker, has at least two electrodes, and a proximal end adapted for electrical and mechanical connection to the active device and a distal end opposite the proximal end. A ventricular electrode is carried at the distal end of the lead for sensing and/or electrical interaction with the ventricle, and an atrial electrode is carried on the lead for sensing and/or electrical interaction with the atrium, the atrial electrode being disposed between the proximal end and the ventricular electrode. The lead at its distal end has a first part with a first predetermined length, which is between 9 and 13 cm, and which exhibits a first stiffness. Adjacent to this first part is a second part, having a second predetermined length, which exceeds 15 cm, and which exhibits a second stiffness. The first stiffness of the first part provides the overall lead with a stiffness so as to force the atrial electrode in contact with the atrial wall when the lead is implanted. The second stiffness is greater then the first stiffness. The lead has a transition point between the first part and the second part, disposed at the proximal end of the second part.

12 Claims, 1 Drawing Sheet

ELECTRODE LEAD WITH TEMPORARY INCREASED STIFFNESS DURING INGROWTH

BACKGROUND OF THE INVENTION

1. Field of the Invention

The present invention relates to a single lead adapted to be used with an implantable active device, such as a pacemaker, in dual pacing and/or sensing.

2. Description Of The Prior Art

Conventionally, dual chamber sensing/pacing has required one lead for the atrium and one lead for the ventricle, i.e. two leads have been implanted into the heart.

Different approaches has been made in order to make possible a good sensing signal from the atrium, which requires essentially a good contact between the sensing/pacing electrode and the inner wall of the atrial cavity. The atrial electrode has for instance been anchored in the atrium or be kept in close contact with the atrial wall mechanically by means applied on the outside of the body until the electrode has been fastened by ingrowth.

More recently, several approaches with single leads have been made.

In German Patentschrift 30 49 652, corresponding to PCT Application WO 80/02801 a bent lead is described which partly has the form of a spiral. The entire bent part has a form that is adapted to the inner cavity wall of the atrium. Apart from the bent part there is a second part which may have a dimension which is smaller than the dimension of the bent part. The shape of the bent part is such that a part thereof is kept in contact with the atrial wall. When the lead is in place it will be kept there until a layer of fibrin has covered the lead, which means that the lead actually will be fastened to the atrial wall.

Another solution is described in U.S. Pat. No. 4,154,247 in which the lead comprising a layer of a repeatable thermally-activated material, is heated before implantation and thereafter the lead is shaped into a non-linear configuration, reforming the lead into a linear configuration, inserting the lead to make electrical contact with the body organ and discontinuing the straightening of the pacer lead. Thus the lead is devised with more geometric variations at the atrial electrode. For example in one embodiment the electrode lead is laid in a circle to enable the atrial electrode to establish continuous contact with atrial tissue.

Yet another solution is described in the U.S. Pat. No. 5,476,499 where a single lead having an atrial electrode at a distal end for implantation in the atrium before the electrode lead is advanced deeper into the heart so a ventricular electrode in-line with and preceding the atrial electrode along the lead, is connectable in the ventricle of the heart. The ventricular electrode is affixed to the ventricular trabecular network. The part of the electrode distal to the ventricular electrode, i.e. the part between the ventricular electrode and the atrial electrode is made significantly thinner than the rest of the electrode lead. This lead has to pass through the tricuspid valve twice.

The greater part of the atrium inner wall from the vena cava superior and downwards does not exhibit any trabecular network which conventionally may be used for the fastening of the electrode or electrodes the wall is smooth.

SUMMARY OF THE INVENTION

An object of the invention is to achieve a lead which can easily be implanted in a heart and which simply and effectively ensures electrical contact between atrial tissue and the atrial electrode/-s.

The above object is achieved in accordance with the principles of the present invention in an implantable lead for an active implantable device, such as a pacemaker, the lead having a proximal end adapted for electrical and mechanical connection to the device and a distal end opposite the proximal end, with a ventricular electrode carried on the lead at the distal end and an atrial lead carried on the electrode between the proximal end of the lead and the ventricular electrode, wherein the distal portion of the lead has a first part with a first predetermined length between 9 and 13 cm and having a first stiffness, with a second part adjacent to the first part exhibiting a second predetermined length which exceeds 15 cm and having a second stiffness, the second stiffness of the second part: providing the overall lead with a stiffness so as to force the atrial electrode into contact with the atrial wall when implanted, and the second stiffness being greater then the first stiffness. The lead further has a transition point between the first and second parts, at a proximal end of the first part. The second part has a radius of curvature which exceeds 20 cm. Preferably the length of the second part is 25 cm and the radius of curvature of the second part is 25 cm.

In contrast to the previously described electrode leads of the ventricular tip and atrial electrode type the present invention takes the specific anatomy of the atrium into account for anchoring the atrial electrode in the atrial tissue.

It fixes the atrial electrode in a simple and secure manner such that the electrode will achieve efficient electrical contact with the atrial wall.

The atrium comprises a specific site on the lower atrial wall that is situated inferior to the exit of the coronary sinus. The inventors have found that this site may be used in the implantation of the atrial electrode. According to the invention, it has been shown that a lead, as defined above, which has a stiffer portion with a length of more than approximately 15 cm and which is situated proximal and adjacent to a part of the lead with a lesser stiffness and a length of approximately 9–13 cm at the distal end of the lead, when implanted in the heart will easily be placed in such a position that the transition point between the two parts with different stiffness will stay in the above defined site.

The less stiff, distal part of the lead should be very flexible with a length of approximately 9–13 cm in order to avoid mechanical forces on the atrial electrode(s) being transferred from the distal part, for instance caused by the movements of the heart. The stiffer proximal portion of the lead should be straight or at least have a radius of curvature exceeding 20 cm in the non-implanted and non-loaded condition of the lead. It should be noted that the minimum stiffness of the proximal part of the lead is stiff in an assymmetrical way, the minimum stiffness of the proximal part should exceed the stiffness of the proximal part. It is however preferred that the stiffness of the lead is symmetrical, i. e. that the lead has the same stiffness in all directions.

The portion of the lead in the subclavian vein, in vena cava superior and in the atrium above this defined site is thus according to the invention intentionally made stiff, and for this reason the ring electrode(s) will be forced in contact with atrial tissue during the ingrowth period. Direct contact will provide good pacing and sensing performance and is also necessary for the electrode ingrowth.

The implantation of the lead is conducted using a stylet and as a first measure the lead having the ventricular electrode at the distal end thereof is introduced and fastened at the appropriate place in the ventricle. The stylet is then retracted to a position proximal to the transition point. The lead will then move outwardly against the atrial wall since the stiff part, which is deflected by the veins and the atrium into a curve having a smaller radius of curvature than the radius of curvature in the non-implanted condition, will strive to resume its original, straighter shape because of its inherent greater stiffness. The transition point then can will then be placed in, or can easily be slid along the atrial wall into, the site above described as being located inferior to the coronary sinus.

To avoid long term irritation the inflexibility/stiffness of the proximal part of the lead is preferably made to decline in about a week when the ring is fixed. This can be attained by using an inner or outer polymer in the lead of the type which softens by time in the body due increased temperature or water content. Alternatively the lead be a standard lead covered with an additional layer of bioresorbable material initially stiffening the lead. When this layer has been resorbed, the lead will revert to the flexsibility of a standard lead. The kind of material in and the thickness of the layer is chosen such that the lead will keep its stiffness until the electrode has become attached to the atrial wall.

To facilitate ingrowth of the electrode other measures may be taken to improve the ingrowth, e.g. a small dummy ring made of a material which is known to easily grow into the tissue can be placed near the sensing and/or stimulation atrial electrode. The electrode itself can also be made of material that adsorbs plasma proteins and accelerates the ingrowth. Examples of such material are carbon and gold.

DESCRIPTION OF THE PREFERRED EMBODIMENTS

Figure 1A:
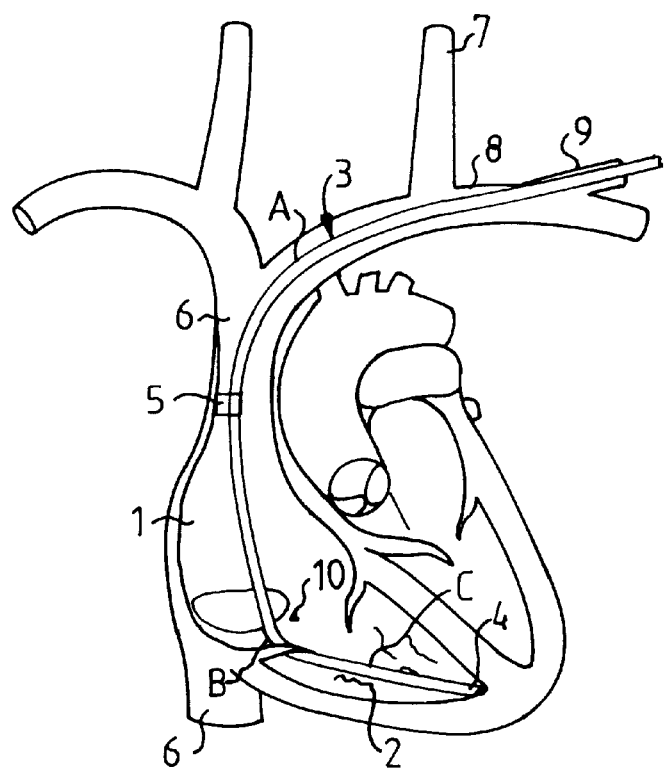
FIG. 1A shows a first embodiment of a lead according to the invention implanted in a heart.
Figure 1B:
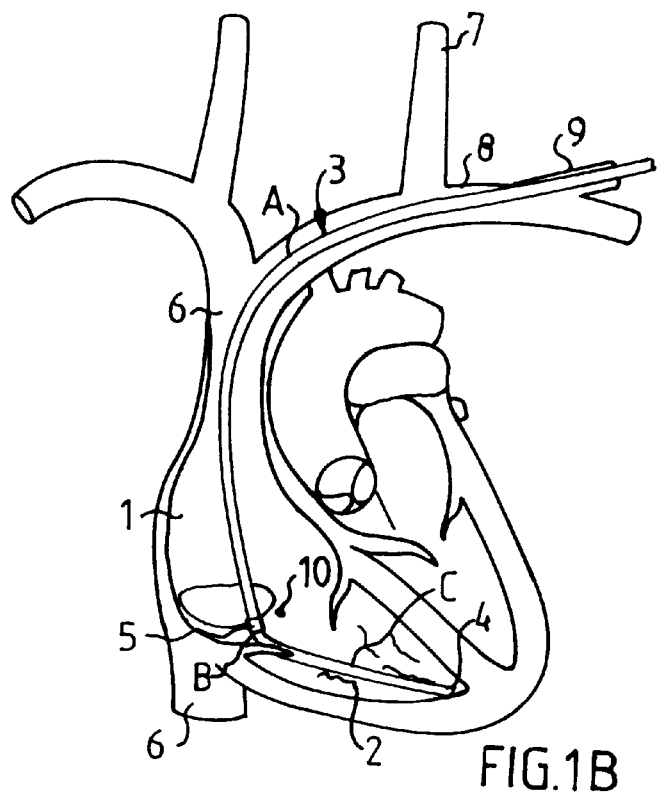
FIG. 1B shows a second embodiment of a lead according to the invention implanted in a heart.

FIGS. 1A and 1B show two alternative implantation configurations for the lead according to the invention. In both figures the same numbers are used to denote equivalent details.

In FIG. 1A the right atrium 1 and the right ventricle 2 is shown. The lead 3 enters the atrium through the superior vena cava 6. The lead may for instance be introduced into the superior vena cava though the left internal jugular vein, the left external jugular vein 7, the left subclavian vein 8 or the cephalic vein 9. The tip electrode 4 at the distal end of the lead is shown near the apex of the heart and the ring electrode 5 at the inner wall of the myocardium in the lower part of the atrium, in the site defined above as inferior to the exit of the coronary sinus. In order to keep the ring electrode 5 in place during the ingrowth period the part proximal and adjacent to the ring electrode 5, part A, is intentionally made stiff. There thus is a transition point (B) in the lead between the stiffer part A and the distal part C of the lead An illustration of the advantages of the above preferred embodiment is that the amplitude of the P-wave in an electrogram, as measured with the atrial electrode, is 16 mV and the slew rate (the signal's change in amplitude per unit of time, usually expressed in V/s) 3V/s, as measured by the electrode at the transition point B at the location below the exit of the coronary sinus. These are extraordinary good values for the atrium (the slew rate gives an indication as to how well the peak will be seen in the electrogram).

The lead shown in FIG. 1B is identical to the lead shown in FIG. 1A apart from the location of the atrial electrode. The atrial electrode here is placed a distance of 3–5 cm from the transition point and proximal thereto. Again the right atrium 1 and the right ventricle 2 are shown. The lead 3 enters the atrium through the superior vena cava. The tip electrode 4 at the distal end of the lead is shown near the apex of the heart and the ring electrode 5 at the inner wall of the myocardium near the opening of the vena cava into the atrium. In order to keep the ring electrode 5 in place during the ingrowth period, part of the lead proximal and immediately distal to the ring electrode 5 up to the transition point B, part A, is intentionally made stiff such that the transition point (B) between the lead parts with different stiffness again will be placed in the site defined as inferior to the exit of the coronary sinus. The electrode will be forced against the atrial wall in the same manner as the electrode located it the transition point as described above.

The stiffness in part A is greater than the stiffness of a conventional bipolar lead proximal to the ring electrode. A conventional bipolar lead has a diameter of approximatively 1–2.5 mm proximal in relation to the ring as compared to the lead according to the invention has an approximal diameter of 1–3 mm.

The lead according to the invention exerts a force in the direction of the normal to the atrial wall at the transisiton point of approximatively 25 mN, whereas the force generally exerted against the atrial wall of by a conventional bipolar lead, if in contact with the wail, would be about 5–6 mN. The force exerted by the lead according to the invention is far below the practical upper limit at which there could be a risk for penetration of the atrial wall.

The manner in which the inflexibility/stiffness of the lead may be achieved may be to make this part at least partly from a less flexibility/thicker material. A temporary inflexibility/stiffness of the lead, which is pregnable, may also be achieved by placing a material of liquid absorbing material changing the characteristics on the absorption of liquid within or outside the lead outer cover. To place the liquid absorbing material inside the outer cover is made possible on account of the ability of the cover material on the lead, which preferable is silicon, to allow water to be transported through the material . Other biocompatible materials having the same characteristics are of course possible to use instead. An alternative could be to cover a standard lead with a layer of bioresorbable material imparting said stiffness to the lead. When the bioresorbable material has been resorbed, the lead will have the same flexibility as a standard lead.

The portion of the lead distal to the moderately stiff part of the lead, part C, i.e. mainly the part of the lead placed in the ventricle should be highly flexible in order to avoid mechanical forces on the atrial electrode(s). Also the length of this part of the lead may be longer than the actual distance between the implantation site of the atrial electrode and the apex of the heart in order not to put any extra strain on the atrial electrode.

The lead can replace all bipolar leads using two leads each having one electrode (one for the atrium and one for the ventricle) In particular it may be used in bipolar DDD-systems, performing all DDD functions. If used with a pacemaker having an indifferent electrode connected either on the housing or intracorporally, but outside the heart, the pacemaker can also utilized in a unipolar mode.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable lead for an implantable active device, comprising at least two electrodes and having a proximal end adapted for electrical and mechanical connection to said active device, and a distal end opposite said proximal end, a ventricular electrode carried at the distal end of said lead for sensing and/or electrical interaction with a ventricle an atrial electrode carried on said lead for sensing and/or electrical interaction with an atrium, said atrial electrode being disposed between the proximal end and said ventricular electrode, a first part disposed at the distal end and having a first predetermined length, between 9–13 cm, and exhibiting a first stiffness, and a second part, disposed adjacent to said first part said a second part having a second predetermined length which exceeds 15 cm, and a second stiffness, said second stiffness of said second part producing a stiffness adapted to force the atrial electrode in contact with an atrial wall when implanted, said second stiffness being greater than said first stiffness, and a transition point between said first part and said second part situated at the proximal end of said first part, said second part having a radius of curvature exceeding 20 cm.

2. An implantable lead according to claim 1, wherein said atrial electrode is disposed at the transition point.

3. An implantable lead according to claim 1, wherein said atrial electrode is disposed at a position 3–5 cm proximal to the transition point.

4. An implantable lead according to claim 1 wherein said second stiffness minimizes mechanical loads on the ventricular electrode after implantation.

5. An implantable lead according to claim 1 wherein said second stiffness of the second part is a temporary stiffness which decreases a predetermined time after an ingrowth time of the atrial electrode.

6. An implantable lead according to claim 1 further comprising an ingrowth promoting agent carried by said lead to promote ingrowth of the atrial electrode.

7. An implantable lead according to claim 1 wherein said second part has an infinite radius of curvature.

8. An implantable lead according to claim 1 wherein said second part has a shape and dimensions to impart a force below 30 mN to an atrial wall when implanted.

9. An implantable lead as claimed in claim 1 wherein said second predetermined length of said second part is 25 cm.

10. An implantable lead as claimed in claim 1 wherein said second part has a radius of curvature of 25 cm.

11. An implantable lead as claimed in claim 1 wherein said second predetermined length of said second part is 25 cm and wherein said radius of curvature of said second part is 25 cm.

12. An implantable lead as claimed in claim 1 wherein said atrial electrode is comprised of electrode material which promotes ingrowth of said atrial electrode.

* * * * *